United States Patent [19]

Spietschka et al.

[11] Patent Number: 4,594,420
[45] Date of Patent: Jun. 10, 1986

[54] PERYLENE-3,4,9,10-TETRACARBOXYLIC ACID MONOANHYDRIDE MONOIMIDE AND MONOIMIDAZOLIDE COMPOUNDS, PROCESSES FOR THEIR PREPARATION AND THEIR USE

[75] Inventors: Ernst Spietschka, Idstein/Taunus; Helmut Tröster, Königstein/Taunus, Fed. Rep. of Germany

[73] Assignee: Hoechst Aktiengesellschaft, Frankfurt am Main, Fed. Rep. of Germany

[21] Appl. No.: 588,541

[22] Filed: Mar. 12, 1984

[30] Foreign Application Priority Data

Mar. 14, 1983 [DE] Fed. Rep. of Germany ....... 3309060

[51] Int. Cl.$^4$ .................. C07D 491/06; C09B 5/62
[52] U.S. Cl. ....................... 546/29; 546/37; 546/41
[58] Field of Search ..................... 546/29, 37, 41

[56] References Cited

U.S. PATENT DOCUMENTS 1,924,090  8/1933  Eckert .................... 546/41
3,871,882  3/1975  Wiedemann ............... 546/37

FOREIGN PATENT DOCUMENTS 39482 11/1981 European Pat. Off. ........... 546/37

Primary Examiner—George F. Lesmes
Assistant Examiner—S. A. Gibson
Attorney, Agent, or Firm—Connolly and Hutz

[57] ABSTRACT

Compounds of the formula

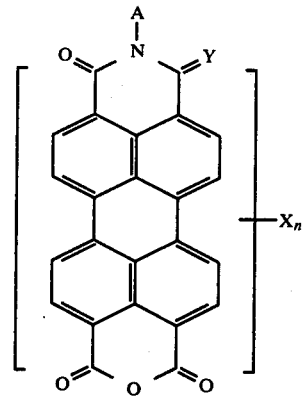

wherein X denotes a chlorine or bromine atom, n denotes a number from zero to 4 and Y denotes an oxygen atom or a nitrogen atom, and A, if Y represents an oxygen atom, is the phenyl radical, which can be substituted by substituents from the group comprising halogen, $C_1$-$C_4$-alkyl, $C_1$-$C_4$-alkoxy, carbalkoxy with 1–4 carbon atoms in the alkyl radical, hydroxyl, carboxyl, $CF_3$, nitro, phenoxy, phenoxy which is substituted by $C_1$-$C_4$-alkyl, $C_1$-$C_4$-alkoxy and/or halogen, phenylamino, phenylamino which is substituted in the phenyl radical by $C_1$-$C_4$-alkyl, $C_1$-$C_4$-alkoxy and/or halogen, phenylazo and phenylazo which is substituted by $C_1$-$C_4$-alkyl, $C_1$-$C_4$-akloxy and/or halogen, or is the pyridyl radical, which can be substituted by halogen and/or $C_1$-$C_4$-alkyl, or A, if Y represents a nitrogen atom, is the o-phenylene radical, which, together with Y and the other nitrogen atom, forms the benzimidazole ring, it being possible for the benzene nucleus of the benzimidazole ring to be substituted by substituents from the group comprising halogen, $C_1$-$C_4$-alkyl and $C_1$-$C_4$-alkoxy, processes for their preparation and their use as colorants or their use as intermediates for the preparation of colorants.

7 Claims, No Drawings

PERYLENE-3,4,9,10-TETRACARBOXYLIC ACID MONOANHYDRIDE MONOIMIDE AND MONOIMIDAZOLIDE COMPOUNDS, PROCESSES FOR THEIR PREPARATION AND THEIR USE

The invention relates to the technical field of the preparation of dyestuffs and pigments.

Perylene-3,4,9,10-tetracarboxylic acid monoanhydride monoalkylimide compounds are already known from European Patent Application Publication No. 0,039,482-A, but corresponding monoimide-monoanhydrides cannot be prepared, or can be prepared only with difficulty and in exceptionally low yields, by the process described therein, using weakly basic amines as alkylamines.

By the present invention, new perylene-3,4,9,10-tetracarboxylic acid monoanhydride monoimide compounds of the general formula (1)

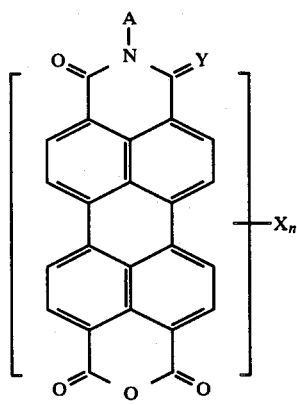

have now been found, in which the individual members of the formula have the following meanings:

X is a chlorine or bromine atom;
n is a number from zero to 4;
Y represents an oxygen atom or a nitrogen atom;
A, if Y represents an oxygen atom, is the phenyl radical, which can be substituted by substituents from the group comprising halogen, such as iodine, fluorine and, in particular, chlorine and bromine, alkyl of 1 to 4 carbon atoms, alkoxy of 1 to 4 carbon atoms, carbalkoxy with 1 to 4 carbon atoms in the alkyl radical, such as carbomethoxy and carbethoxy, hydroxyl, carboxyl, trifluoromethyl, nitro, phenoxy, phenoxy which is substituted by alkyl of 1 to 4 carbon atoms, alkoxy of 1 to 4 carbon atoms and/or halogen, such as chlorine and bromine, phenylamino, phenylamino which is substituted in the phenyl radical by alkyl of 1 to 4 carbon atoms, alkoxy of 1 to 4 carbon atoms and/or halogen, such as chlorine and bromine, phenylazo and phenylazo which is substituted by alkyl of 1 to 4 carbon atoms, alkoxy of 1 to 4 carbon atoms and/or halogen, such as chlorine and bromine, or A is the pyridyl radical, which can be substituted by halogen, such as bromine and chlorine, and/or alkyl of 1 to 4 carbon atoms, such as ethyl and, in particular, methyl, or A, if Y represents a nitrogen atom, is the ortho-phenylene radical, which, together with Y and the other nitrogen atom, forms the benzimidazole ring, it being possible for this o-phenylene radical to be substituted by substituents from the group comprising halogen, such as chlorine and bromine, alkyl of 1 to 4 carbon atoms and alkoxy of 1 to 4 carbon atoms.

Examples of alkyl groups of 1 to 4 carbon atoms are the methyl group and the ethyl group; examples of alkoxy groups of 1 to 4 carbon atoms are the methoxy group and the ethoxy group. The substituents in the formula radical A can be 1-, 2- or 3-substituents.

Preferred compounds of the general formula (1) are those in which Y denotes an oxygen atom and A denotes the phenyl radical, which can be substituted by substituents from the group comprising alkyl of 1 to 4 carbon atoms, alkoxy of 1 to 4 carbon atoms, chlorine and bromine, or in which Y represents a nitrogen atom and A denotes the o-phenylene radical, which can be substituted by one or two substituents from the group comprising alkyl of 1 to 4 carbon atoms, alkoxy of 1 to 4 carbon atoms and chlorine.

Those compounds of the general formula (1) in which n denotes the number zero are furthermore preferred.

The preferred invention furthermore relates to a process for the preparation of the new compounds of the general formula (1), which comprises reacting the tetrasalt of perylene-3,4,9,10-tetracarboxylic acid of the general formula (2)

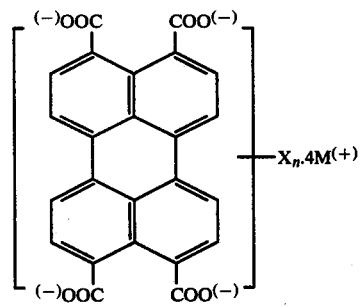

in which X and n have the abovementioned meanings and $M^{(+)}$ is the ammonium ion of a secondary or, preferably, tertiary amine which is capable of establishing a pH value of 8.5 or higher in aqueous solution, and an aromatic amino compound of the general formula (3) or (4)

$$B-NH_2 \qquad (3)$$

$$H_2N-D-NH_2 \qquad (4)$$

in which B denotes the optionally substituted phenyl or pyridyl radical mentioned above for A and D represents the ortho-phenylene radical which, as indicated above for A, can be substituted by substituents from the group comprising halogen, alkyl of 1 to 4 carbon atoms and alkoxy of 1 to 4 carbon atoms, with one another in aqueous or aqueous-organic solution, this reaction solution initially being adjusted to a pH value of between 7 and 5, preferably between 6.8 and 6.2, by addition of acid, advantageously by gradual addition of acid, at room temperature or elevated temperature, such as at a temperature between 10° C. and the boiling point of the reaction mixture, preferably between 15° and 95° C., and the reaction then being carried out within the given pH range at elevated temperature, preferably at a temperature between 70° C. and the boiling point of the reaction medium, such as between 70° and 110° C.

The reaction of the compounds of the general formula (2) with the amines of the general formula (3) or (4) is carried out using equimolar amounts, a slight excess of the amine (3) or (4) being advantageous. This excess can be up to 20 mole %, depending on the amine employed as a reactant, in particular on the basicity of the amine.

The aqueous-organic reaction medium contains, as the organic solvent component, for example, dimethylformamide or an unsaturated tertiary amine, such as, in particular, a picoline or pyridine. In a preferred embodiment, the process according to the invention is carried out in an aqueous-organic reaction medium using a picoline or pyridine as the organic solvent component. These unsaturated tertiary amines can serve as buffers and solubilizing agents for the reactants in the reaction batch; the amount of this organic solvent component can here be varied within wide limits. 10 to 80% of the unsaturated tertiary amine, based on the amount of water used in the reaction solution, is preferably employed. The unsaturated tertiary amine is advantageously added to the aqueous reaction solution before the pH range of between 7 and 5 is established.

The ammonium ion $M^{(+)}$ in the starting compounds of the general formula (2) is preferably an ammonium ion of the general formula (5)

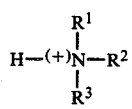

(5)

in which $R^1$, $R^2$ and $R^3$ can have meanings which are identical to one another or which differ from one another, and $R^1$ denotes a hydrogen atom or an alkyl group of 1 to 4 carbon atoms, preferably a methyl or ethyl group, which can be substituted by a hydroxyl group, $R^2$ denotes an alkyl group of 1 to 4 carbon atoms, such as the methyl or ethyl group, which can be substituted by a hydroxyl group, and $R^3$ is an alkyl group of 1 to 4 carbon atoms, such as the methyl or ethyl group, which can be substituted by a hydroxyl group, or in which $R^2$ and $R^3$, together with the nitrogen atom, form a saturated, heterocyclic ring which optionally contains an oxygen atom or a nitrogen atom as a further heteroatom. Examples of corresponding secondary or tertiary amines which are suitable for this ion are dimethylamine, diethylamine, dibutylamine, diethanolamine, triethanolamine, trimethylamine, triethylamine, piperidine and morpholine, and of these, trimethylamine is preferred and triethylamine is particularly preferred.

Examples of aromatic amines (3) which serve as starting compounds are aniline, 2-methyl-aniline, 3-methyl-aniline, 4-methyl-aniline, 3,5-dimethyl-aniline, 2,4-dimethyl-aniline, 2,5-dimethyl-aniline, 2,6-dimethyl-aniline, 3,4-dimethyl-aniline, 4-isopropyl-aniline, 2,4,6-trimethyl-aniline, 2-chloro-aniline, 3-chloro-aniline, 4-chloro-aniline, 2,4-dichloro-aniline, 3-bromo-aniline, 3-iodo-aniline, 2-methyl-5-chloro-aniline, 3-chloro-4-methyl-aniline, 3-trifluoromethyl-aniline, 3,5-bis-(trifluoromethyl)-aniline, 2-aminophenol, 3-aminophenol, 4-methoxy-aniline, 4-ethoxy-aniline, 2-amino-1,4-dimethoxy-benzene, 4-amino-diphenyl ether, 4-amino-4'-chloro-diphenyl ether, 4-amino-diphenylamine, 4-amino-azobenzene, 3-nitro-aniline, dimethyl 5-aminoisophthalate, 3-aminobenzoic acid, 2-aminopyridine and 3-aminopyridine.

Examples of amino compounds of the general formula (4) which serve as starting compounds are 1,2-diaminobenzene, 4-methyl-1,2-diaminobenzene, 4-methoxy-1,2-diaminobenzene, 4-chloro-1,2-diaminobenzene and 4,5-dichloro-1,2-diaminobenzene.

The process according to the invention can be carried out, for example, by first treating the perylenetetracarboxylic acid or its dianhydride, in water, with the amount of amino compound, which should be capable of establishing a pH value of 8.5 or more in water, required for conversion into the tetracarboxylate, in the customary manner at elevated temperature. A slight excess, such as up to 10% of the amine, i.e. up to 4.4 moles of this amine per mole of perylenetetracarboxylic acid or its dianhydride, is advantageously employed. The amine of the general formula (3) or (4) and, if appropriate, an unsaturated tertiary amine, such as pyridine, as the organic solvent component, are then added and a pH value within the abovementioned pH range is then established by addition of acid. Acids which can be used for this are inorganic and organic acids, thus, for example, mineral acids, such as hydrochloric acid or sulfuric acid, but preferably, because of their buffer action, moderately strong to weak organic or inorganic acids, such as, for example, formic acid, acetic acid, propionic acid, carbonic acid or phosphoric acid. The batch is then warmed and the given pH range is maintained by addition of further acid, since the pH value otherwise rises during the reaction.

The reaction product formed is isolated by acidification of the reaction mixture and filtration in a manner which is customary per se. The diimide or bis-benzimidazole compound which is also formed and is insoluble in alkali is removed by addition of alkali and by filtration. Any unreacted perylenetetracarboxylic acid still contained in the product can be removed from the potassium salt of the end product according to the invention, which is usually sparingly soluble, via its readily soluble tetrapotassium salt.

The new compounds of the general formula (1) according to the invention are useful starting substances for the preparation of colorants (dyestuffs and pigments), such as symmetric or asymmetric N-substituted perylene-3,4,9,10-tetracarboxylic acid diimides (cf., for example, Chemistry Letters 1979, 151–154). However, they can themselves also be used as colorants, such as, for example, in lacquers or for dyeing polymers, such as polyolefins and polyvinyl chloride, if necessary after appropriate conditioning.

The examples which follow serve to illustrate the invention in more detail. The parts are by weight and the percentage are by weight, unless indicated otherwise. Parts by weight bear the same relationship to parts by volume as that of the kilogram to the liter.

EXAMPLE 1

39.2 parts of perylene-3,4,9,10-tetracarboxylic acid dianhydride are dissolved in a mixture of 500 parts of water and 44.5 parts of triethylamine at 90° C. After addition of 12.3 parts of 3,5-dimethylaniline, a pH value of between 6.3 and 6.6 is established with 85% strength aqueous phosphoric acid. Stirring is continued at 90° C. for 6 hours, during which the given pH range is maintained by dropwise addition of further phosphoric acid; a total of about 33 parts of 85% strength phosphoric acid are consumed.

When the reaction has ended, a further 20 parts of 85% strength phosphoric acid are added and the reaction product which has precipitated is filtered off with suction and washed first with 2% strength aqueous hydrochloric acid and then with water until free from acid.

To remove unreacted perylenetetracarboxylic acid and the diimide also formed, the procedure is as follows: the moist filter cake is stirred in 1,500 parts of 5% strength aqueous potassium hydroxide solution at 90° to 95° C. for two hours and the solid is then filtered off with suction at 20° to 25° C. and washed with 5% strength aqueous potassium hydroxide solution until the filtrate runnings are colorless. The filter cake is then treated with hot water, whereupon the dipotassium salt of perylenetetracarboxylic acid mono-(3,5-dimethylphenyl)-imide dissolves giving a solution deep red-violet in color.

The insoluble diimide is removed by filtration and the compound according to the invention is precipitated by acidifying the filtrate and isolated.

After drying, the compound of the formula

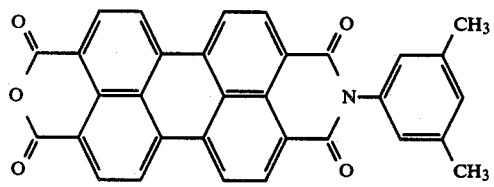

is obtained as a dark red powder.

Yield: 38.7 parts (78.2% of theory).

Analysis ($C_{32}H_{17}NO_5$): calculated: C 77.6%; H 3.4%; N 2.8%; found: C 77.3%; H 3.6%; N 3.0%.

mass spectroscopy: $M^+ = 495$.

EXAMPLE 1a

The procedure described in Example 1 is followed, but the corresponding amount of concentrated aqueous hydrochloric acid is used to establish the pH instead of the phosphoric acid. The product according to the invention is obtained in a similarly good quality in a yield of 40% of theory.

EXAMPLE 1b

The procedure described in Example 1 is followed, but the corresponding amount of acetic acid is used for establishing the pH instead of the phosphoric acid. The compound according to the invention is obtained in a similarly good quality in a yield of 61% of theory.

EXAMPLE 2

78.4 parts of perylene-3,4,9,10-tetracarboxylic acid dianhydride are dissolved in a mixture of 800 parts of water and 89.9 parts of triethylamine at 90° C. 200 parts by volume of pyridine and 26.7 parts of 3,5-dimethylaniline are then added, the mixture is cooled to 20° to 25° C. and a pH value of 6.5 is established at this temperature with 85% strength aqueous phosphoric acid. The reaction batch is then warmed to 90° C., whilst maintaining a pH range of 6.3 to 6.6, and the reaction is carried out at this temperature and within this pH range for 6 hours. A total of about 82 parts of 85% strength aqueous phosphoric acid is consumed.

When the reaction has ended, 400 parts by volume of a pyridine/water mixture is distilled off from the batch, this batch is then acidified with concentrated aqueous hydrochloric acid above 80° C. and the monoxylidide according to the invention is isolated, the diimide also formed and the perylenetetracarboxylic acid being removed by a procedure analogous to that described in Example 1.

The compound according to the invention given in Example 1 is obtained in the same quality in a yield of 89.9 parts (corresponding to 90.8% of theory).

EXAMPLE 3

A solution, prepared at 90° C., of the tetraammonium salt obtained from 39.2 parts of perylene-3,4,9,10-tetracarboxylic acid dianhydride and 38.3 parts of morpholine in 400 parts of water is combined with a solution of 13.3 parts of 3,5-dimethyl-aniline in 200 parts by volume of pyridine. About 40 parts of acetic acid are added to this reaction batch at 90° C. in the course of 6 hours, in order to establish and maintain a pH range of 7 to 6.

When the reaction has ended, 400 parts by volume of liquid are distilled off from the reaction batch, with simultaneous addition of 200 parts of water; the batch is acidified with concentrated aqueous hydrochloric acid and worked up by the procedure described in Example 1.

The monoxylidide according to the invention is obtained in about the same good quality and a yield of 81.8% of theory.

EXAMPLE 3a

If the procedure described in Example 3 is followed, but the tetrapiperidinium or tetra-(trimethylammonium) salt of the perylenetetracarboxylic acid is used instead of its tetramorpholinium salt, the monoxylidide according to the invention which is described in Example 1 by way of its formula is obtained in equally good quality and in about an equally high yield.

EXAMPLE 4

A solution of 20.5 parts of aniline in 200 parts by volume of 4-picoline is allowed to run into a solution, prepared at 80° C., of 78.4 parts of perylene-3,4,9,10-tetracarboxylic acid dianhydride in 740 parts of water and 100 parts of 40% strength aqueous dimethylamine. A pH value of 6.5 is then established at a temperature of 20° to 25° C. by addition of 85% strength aqueous phosphoric acid and the reaction is brought to completion by heating at 90° C. for 3 hours, whilst maintaining a pH range of 6.7 to 6.3.

The monoanilide monoanhydride compound according to the invention which corresponds to the general formula (1a)

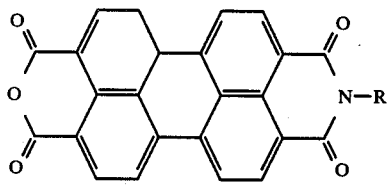

in which R here represents the phenyl radical, is separated off from the reaction batch and isolated by a procedure analogous to that described in Example 1.

Yield: 60.3 parts (64.6% of theory).

Analysis ($C_{30}H_{13}NO_5$): calculated: N 3.0%, found: N 3.2%.

mass spectroscopy: $M^+ = 467$.

EXAMPLE 5

1,000 parts by volume of pyridine and then 75.5 parts of 4-ethoxy-aniline are added to a solution of the tetra-(triethylammonium) salt of perylenetetracarboxylic acid prepared from 196 parts of perylene-3,4,9,10-tetracarboxylic acid dianhydride, 2,000 parts of water and 222 parts of triethylamine, and the mixture is warmed to 90° C. The initial pH value of 8.2 is adjusted to 7.0 with about 40 parts of acetic acid and a further 160 parts of acetic acid are slowly added at the reaction temperature of 90° C. in the course of 6 hours, whereupon the pH value falls from 7.0 to 6.0.

When the reaction has ended, 2,000 parts by volume of liquid are distilled off from the batch, whilst being simultaneously replenished with 1,000 parts of water, and 300 parts by volume of aqueous concentrated hydrochloric acid are then added. The dark red perylenetetracarboxylic acid monoanhydride mono-(4-ethoxyanilide) according to the invention is separated off from the acid suspension by procedure analogous to that described in Example 1.

Yield: 196 parts (76.7% of theory).

Analysis ($C_{32}H_{17}NO_6$): calculated: N 2.7%, found: N 2.9%.

mass spectroscopy: $M^+ = 511$.

The structure of the compound according to the invention corresponds to the general formula (1a) given in Example 4, in which R represents the p-ethoxyphenyl radical.

EXAMPLE 6

To prepare a compound according to the invention, the procedure of Example 5 is followed, but 98.9 parts of 4-methyl-aniline are used instead of the 4-ethoxy-aniline. Perylene-3,4,9,10-tetracarboxylic acid monoanhydride mono-(4-methyl-anilide), corresponding to the general formula (1a) given in Example 4, with R as the 4-methylphenyl radical, is obtained in a yield of 71.4% of theory.

Analysis ($C_{31}H_{15}NO_5$): calculated: N 2.9%, found: N 3.2%.

mass spectroscopy: $M^+ = 481$.

EXAMPLE 7

A solution of 27.0 parts of 4-methoxy-aniline in 100 parts by volume of pyridine is added to a triethylammonium salt solution, prepared according to Example 2, of perylene-3,4,9,10-tetracarboxylic acid, and 78 parts of 85% strength aqueous phosphoric acid are added at a temperature of 20° to 25° C.; the pH value thereby falls from an initial 9.8 to 6.3. The resulting yellow suspension is warmed to 90° C. and the reaction is continued at this temperature for a further hour, the pH value initially falling further to about 5.5 and then rising again to a pH value of about 6.5.

After this reaction, the perylene-3,4,9,10-tetracarboxylic acid monoanhydride mono-(4-methyl-anilide) according to the invention, which corresponds to the general formula (1a) given in Example 4, with R as the 4-methylphenyl radical, is separated off from the reaction batch and isolated by the procedure described in Example 1.

Yield: 52.8 parts (53.1% of theory).

Analysis ($C_{31}H_{15}NO_6$): calculated: N 2.8%, found: N 2.6%.

mass spectroscopy: $M^+ = 497$.

EXAMPLE 8

To prepare a compound according to the invention, the procedure described in Example 2 is followed, but 24.0 parts of 2-aminophenol are used as the starting component instead of 3,5-dimethylaniline.

When the reaction has ended, the compound according to the invention is isolated from the batch and separated off from other products as follows: the reaction batch is filtered and the moist filter cake is dissolved hot in 1,000 parts by volume of 5% strength aqueous potassium hydroxide solution. This dark red solution is adjusted to a pH value of between 8.5 and 8.8 with acetic acid. After addition of 100 parts of potassium acetate, the mixture is allowed to cool and the product which has precipitated is filtered off with suction and washed with 10% strength potassium acetate solution until the filtrate runnings are colorless. The residue is dissolved in hot water, the solution is filtered and the perylene-3,4,9,10-tetracarboxylic acid mononanhydride mono-(2-hydroxyphenyl)-imide according to the invention, which has the structure of the general formula (1a) given in Example 4, with R as the 2-hydroxyphenyl radical, is precipitated with dilute sulfuric acid and isolated.

Yield: 80.0 parts (82.8% of theory).

Analysis ($C_{30}H_{13}NO_6$): calculated: N 2.9%, found: N 3.0%.

mass spectroscopy: $M^+ = 483$.

EXAMPLE 9

27.5 parts of dibromo-perylene-3,4,9,10-tetracarboxylic acid dianhydride are dissolved in 222 parts of 10% strength aqueous triethylamine at 80° C. 6.7 parts of 3,5-dimethylaniline in 50 parts by volume of pyridine are added to this solution and this batch is adjusted to a pH value of between 6.4 and 6.6 with 85% strength aqueous phosphoric acid and stirred at 90° C. for a further 10 hours, whilst maintaining this pH range by means of phosphoric acid.

When the reaction has ended, the batch is acidified with concentrated aqueous hydrochloric acid and the compound according to the invention is isolated by the procedure described in Example 1.

Yield: 10.6 parts (32.5% of theory).

Analysis ($C_{32}H_{15}Br_2NO_5$): calculated: Br 24.5%, N 2.1%, found: Br 21.8%, N 2.2%.

mass spectroscopy: $M^+ = 653$.

The compound according to the invention prepared here has the following structure:

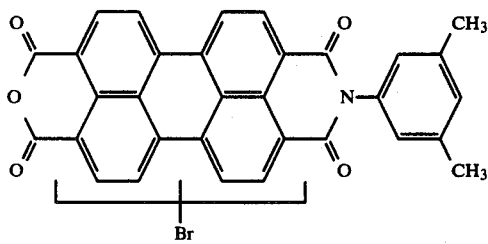

EXAMPLE 10

39.2 parts of perylene-3,4,9,10-tetracarboxylic acid dianhydride are dissolved hot in 500 parts of water and 44.5 parts of triethylamine. 400 parts by volume of pyridine and 32.4 parts of 1,2-diaminobenzene are added. 26 parts of acetic acid are then added at a reaction temperature of 90° C. in the course of 2 hours; during this addition, the pH value falls from an initial 7.7 to 5.9 Stirring is continued at 90° C. for a further 2 hours, during which the pH value rises to about 6.4. After cooling to 20° to 25° C., the dark violet reaction product is filtered off with suction and washed with water and methanol until free from salts and amine.

To isolate the compound according to the invention, the moist filter cake is stirred in 250 parts of water; 40 parts of 50% strength aqueous potassium hydroxide solution are added and the entire mixture is warmed to 90° C. The dipotassium salt of the monobenzimidazole derivative formed is salted out by addition of 60 parts of potassium acetate. The salt is filtered off with suction at 20° to 25° C. and washed with 18% strength aqueous potassium acetate solution, until it is free from perylene-tetracarboxylic acid. The residue is dissolved in hot water and separated off from the insoluble bis-benzimidazole by-product by filtration. The compound according to the invention is precipitated from the deep violet filtrate under acid conditions using hydrochloric acid and isolated.

Yield: 31.7 parts (68.4% of theory).

Analysis ($C_{30}H_{12}N_2O_4$): calculated: N 6.0%, found: N 5.8%.

mass spectoscopy: $M^+ = 464$.

This compound according to the invention has the following structure:

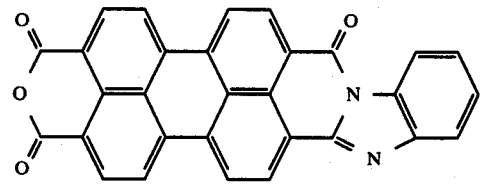

EXAMPLE 11

200 parts by volume of pyridine and 34.0 parts of 4-chloro-1,2-diaminobenzene are added to an aqueous solution, prepared according to Example 2, of the tetra-(triethylammonium) salt of perylene-3,4,9,10-tetracarboxylic acid. This reaction batch is first adjusted to a pH value between 6.6 and 6.4 with 85% strength aqueous phosphoric acid at a reaction temperature of 90° C. and this pH range is maintained over a reaction time of 12 hours at 90° C. by addition of phosphoric acid; a total of about 72 parts of 85% strength aqueous phosphoric acid are required for this.

When the reaction has ended, the batch is worked up as follows: 220 parts of 50% strength aqueous potassium hydroxide solution are added, the mixture is distilled up to a passing-over temperature of 98° C. and then cooled to 20° to 25° C., the solid is filtered off and the residue is washed with 18% strength aqueous potassium acetate solution until the filtrate runnings are colorless. The residue is dissolved in hot water and the insoluble bis-chlorobenzimidazole by-product is separated off by filtration. The isomer mixture of the compounds according to the invention of the formulae

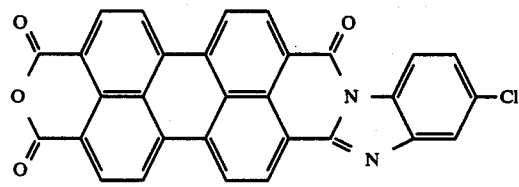

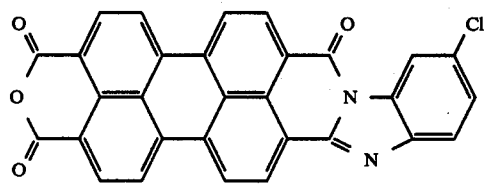

is precipitated from the deep blue-violet filtrate with hydrochloric acid, isolated, washed with water and dried.

Yield: 44.9 parts (45% of theory).

Analysis ($C_{30}H_{11}ClN_2O_4$): calculated: Cl 7.1%; N 5.6%; found: Cl 6.8%; N 5.4%.

mass spectroscopy: $M^+ = 498$.

EXAMPLES 12 TO 28

Further compounds according to the invention corresponding to the general formula (1a) given in Example 4 are described in the following tabular examples, it being possible to prepare these compounds in the manner according to the invention, for example analogously to one of the abovementioned embodiment Examples 1 to 5 or 7, by reacting the tetraammonium salts of perylene-3,4,9,10-tetracarboxylic acid which are used according to the invention with the substituted aniline compounds of the formula R—NH$_2$. Like the compounds according to the invention described in Examples 1 to 9, these products are useful intermediates for the preparation of colorants and themselves have good colorant properties with good fastnesses and technological properties.

Example 31 are described in the tabular Examples 30 and 31. Like the compounds according to the invention described in Examples 10 and 11, these products are useful intermediates for the preparation of colorants and themselves have good colorant properties with good technological properties and fastnesses.

| Example | Compound of the general formula (1) |
|---|---|
| 30 | 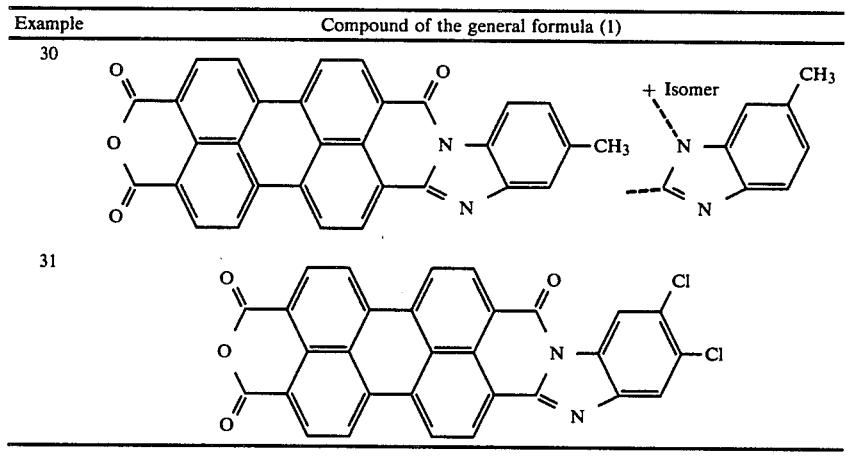 |
| 31 | |

| Ex-ample | R of formula (1a) | Analysis calculated (%) | | found (%) | | M+ |
|---|---|---|---|---|---|---|
| 12 | 2,5-dimethyl-phenyl | N | 2.8 | N | 2.9 | 495 |
| 13 | 3,4-dimethyl-phenyl | N | 2.8 | N | 2.5 | 495 |
| 14 | 4-chloro-phenyl | Cl | 7.1 | Cl | 7.0 | 501 |
| | | N | 2.8 | N | 2.9 | |
| 15 | 3-chloro-phenyl | Cl | 7.1 | Cl | 7.2 | 501 |
| | | N | 2.8 | N | 2.9 | |
| 16 | 3-bromo-phenyl | Br | 14.6 | Br | 15.6 | 545 |
| | | N | 2.6 | N | 2.5 | |
| 17 | 2,4-dichloro-phenyl | Cl | 13.2 | Cl | 12.8 | 535 |
| | | N | 2.6 | N | 2.7 | |
| 18 | 3-trifluoromethyl-phenyl | F | 10.6 | F | 10.2 | 535 |
| | | N | 2.6 | N | 2.6 | |
| 19 | 3,5-bis-(trifluoromethyl)-phenyl | F | 18.9 | F | 18.0 | 603 |
| | | N | 2.3 | N | 2.2 | |
| 20 | 2,4,6-trimethyl-phenyl | N | 2.7 | N | 2.7 | 509 |
| 21 | 2,5-dimethoxy-phenyl | N | 2.7 | N | 2.8 | 527 |
| 22 | 4-(phenoxy)-phenyl | N | 2.5 | N | 2.9 | 559 |
| 23 | 4-(phenylamino)-phenyl | N | 5.0 | N | 5.0 | 558 |
| 24 | 4-(phenylazo)-phenyl | N | 7.4 | N | 7.4 | 571 |
| 25 | pyrid-3-yl | N | 6.0 | N | 5.4 | 468 |
| 26 | pyrid-2-yl | N | 6.0 | N | 5.8 | 468 |
| 27 | 3-hydroxy-phenyl | N | 2.9 | N | 2.6 | 483 |
| 28 | 3-nitro-phenyl | N | 5.5 | N | 5.3 | 512 |
| 29 | 4-bromo-phenyl | Br | 14.6 | N | 14.9 | 545 |
| | | N | 2.6 | | 2.4 | |

EXAMPLES 30 AND 31

Further compounds according to the invention which can be prepared in the manner according to the invention, for example analogously to Example 10 or 11, by reacting the tetraammonium salts of perylene-3,4,9,10-tetracarboxylic acid which are employed according to the invention with 4-methyl-1,2-diaminobenzene for the isomer mixture of Example 30 or with 4,5-dichloro-1,2-diaminobenzene for the compound of

| | Analyses: | | | |
|---|---|---|---|---|
| Example | Calculated (%) | | Found (%) | | M± |
| 30 | N | 5.9 | N | 5.3 | 478 |
| 31 | Cl | 13.3 | Cl | 12.8 | 532 |
| | N | 5.3 | N | 5.2 | |

We claim:

1. A perylene-3,4,9,10-tetracarboxylic acid monoanhydride monoimide compound of the formula (1)

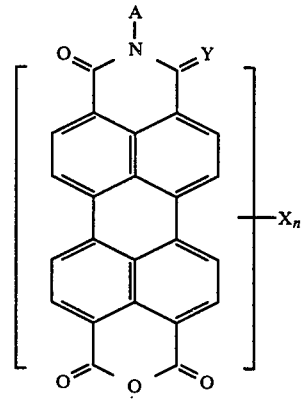

with the following meanings:
wherein X represents chlorine or bromine,
n denotes an integer from 0 to 4,
Y represents an oxygen atom or a nitrogen atom being part of a benzimidazole ring, A, if Y represents an oxygen atom, denotes phenyl being nonsubstituted or substituted by 1 to 3 members of the group consisting of alkyl$_{C_1-C_4}$, alkoxy$_{C_1-C_4}$, hydroxyl, trifluoromethyl and halogen or one member of the group consisting of nitro, phenoxy, phenylamino, phenylazo and pyridyl, or A, if Y represents a nitrogen atom, is the orthophenylene radical which together with the two nitrogen atoms forms the benzimidazole ring, the benzene nucleus of which being non-substituted or substituted by 1 to 2 members of the group consisting of chlorine, alkyl$_{C_1-C_4}$ and alkoxy$_{C_1-C_4}$.

2. A compound as claimed in claim 1, wherein with the formula (1) Y represents an oxygen atom and A represents phenyl unsubstituted phenyl substituted by 1 to 3 members of the group comprising alkyl of 1 to 4 carbon atoms, alkoxy of 1 to 4 carbon atoms, chlorine and bromine.

3. A compound as claimed in claim 1, in which n denotes the number zero Y represents oxygen and A is the 4-bromo-phenyl.

4. A compound as claimed in claim 1, in which Y is an oxygen atom, n denotes the number zero and A is the p-methoxy- or p-ethoxy-phenyl.

5. The compound as claimed in claim 1, in which Y is an oxygen atom, n denotes the number zero and A is the 3,5-dimethyl-phenyl.

6. The compound as claimed in claim 1, in which Y is an oxygen atom, n denotes the number zero and A is the 4-chloro-phenyl.

7. The compound as claimed in claim 1, in which Y is an oxygen atom, n denotes the number zero and A is a methyl-phenyl.

* * * * *